(12) United States Patent
Tian et al.

(10) Patent No.: US 11,432,799 B2
(45) Date of Patent: Sep. 6, 2022

(54) FULLY AUTOMATIC ULTRASONIC SCANNER AND SCAN DETECTION METHOD

(71) Applicant: SoftProbe Medical Systems, Inc., Shanghai (CN)

(72) Inventors: Xudong Tian, Shanghai (CN); Zhifeng Sun, Shanghai (CN)

(73) Assignee: SOFTPROBE MEDICAL SYSTEMS, INC., Shanghai (CN)

( * ) Notice: Subject to any disclaimer, the term of this patent is extended or adjusted under 35 U.S.C. 154(b) by 735 days.

(21) Appl. No.: 15/754,182

(22) PCT Filed: Mar. 10, 2016

(86) PCT No.: PCT/CN2016/076081
§ 371 (c)(1),
(2) Date: Feb. 21, 2018

(87) PCT Pub. No.: WO2017/031977
PCT Pub. Date: Mar. 2, 2017

(65) Prior Publication Data
US 2019/0150895 A1    May 23, 2019

(30) Foreign Application Priority Data

Aug. 25, 2015    (CN) .......................... 201510527764.0

(51) Int. Cl.
*A61B 8/00* (2006.01)
*A61B 8/08* (2006.01)
(Continued)

(52) U.S. Cl.
CPC .......... *A61B 8/4455* (2013.01); *A61B 5/0077* (2013.01); *A61B 8/085* (2013.01);
(Continued)

(58) Field of Classification Search
CPC ... A61B 8/4218; A61B 8/4461; A61B 8/4281; A61B 8/4227
See application file for complete search history.

(56) References Cited

U.S. PATENT DOCUMENTS 3,964,296 A * 6/1976 Matzuk .................... A61B 8/00
73/607
4,232,556 A * 11/1980 Cole ........................ A61B 8/00
73/626
(Continued)

FOREIGN PATENT DOCUMENTS

JP    S58118740 A    7/1983
JP    2007216003 A    8/2007
(Continued)

OTHER PUBLICATIONS

Van Beurden et al., "Effectiveness of Stereoscopic Displays in Medicine: A Review" 3D Research vol. 3, article No. 3, Jan. 2012 (Year: 2012).*
(Continued)

*Primary Examiner* — Colin T. Sakamoto
(74) *Attorney, Agent, or Firm* — Pillsbury Winthrop Shaw Pittman LLP

(57) ABSTRACT

A fully automatic ultrasonic scanner and a scan detection method is provided. The fully automatic ultrasonic scanner comprises: an ultrasonic probe (4); a driving system (5) for driving the ultrasonic probe (4) to move; and a flexible structure on which the ultrasonic probe (4) is mounted, wherein the flexible structure enables the ultrasonic probe (4) to be always along a curve of a skin surface and keep perpendicular to the skin surface during scanning. The flexible structure of the fully automatic ultrasonic scanner has self-adaptive effect, can adjust the scan trace and the probe angle in real time according to different curves of the human body, and ensure that the ultrasonic probe (4) scans
(Continued)

against the skin surface and keeps perpendicular to the skin surface, which improves the quality of the scanned images, so as to enhance the detection rate and accuracy rate of early screening, and reduces the probability of missed diagnosis.

12 Claims, 8 Drawing Sheets

(51) Int. Cl.
*A61B 5/00* (2006.01)
*A61B 8/14* (2006.01)
(52) U.S. Cl.
CPC ............ *A61B 8/0825* (2013.01); *A61B 8/145* (2013.01); *A61B 8/40* (2013.01); *A61B 8/429* (2013.01); *A61B 8/4209* (2013.01); *A61B 8/4218* (2013.01); *A61B 8/4254* (2013.01); *A61B 8/4281* (2013.01); *A61B 8/4416* (2013.01); *A61B 8/4461* (2013.01); *A61B 8/5207* (2013.01); *A61B 8/5253* (2013.01); *A61B 8/565* (2013.01); *A61B 8/4405* (2013.01); *A61B 8/466* (2013.01); *A61B 8/483* (2013.01)

(56) References Cited

U.S. PATENT DOCUMENTS

| | | | | |
|---|---|---|---|---|
| 6,808,495 B2* | 10/2004 | Kelly | ............. | A61B 8/0825 600/443 |
| 7,963,918 B2* | 6/2011 | Park | ............. | A61B 8/4209 600/407 |
| 2002/0062080 A1* | 5/2002 | Okawa | ............. | A61B 8/4461 600/459 |
| 2007/0016060 A1* | 1/2007 | Hwang | ............. | A61B 8/483 600/459 |
| 2008/0021317 A1 | 1/2008 | Sumanaweera | | |
| 2008/0221519 A1* | 9/2008 | Schwach | ............. | A61B 8/4209 604/116 |
| 2009/0024039 A1* | 1/2009 | Wang | ............. | A61B 8/483 600/459 |
| 2009/0088639 A1 | 4/2009 | Maschke | | |
| 2010/0063396 A1* | 3/2010 | Anderson | ............. | A61B 8/462 600/459 |
| 2010/0174185 A1* | 7/2010 | Wang | ............. | A61B 8/14 600/437 |
| 2011/0282208 A1* | 11/2011 | Hyoun | ............. | A61B 8/4461 600/445 |
| 2011/0282212 A1* | 11/2011 | Hyoun | ............. | A61B 8/00 600/459 |
| 2011/0301460 A1* | 12/2011 | Anite | ............. | A61B 8/4461 600/443 |
| 2012/0271173 A1* | 10/2012 | Li | ............. | A61B 8/483 600/443 |
| 2014/0330114 A1* | 11/2014 | Navab | ............. | A61B 5/742 600/424 |
| 2015/0087984 A1* | 3/2015 | Tateyama | ............. | G01S 15/8938 600/443 |
| 2016/0166234 A1* | 6/2016 | Zhang | ............. | A61B 6/502 600/443 |
| 2016/0302759 A1* | 10/2016 | Shi | ............. | A61B 8/14 |
| 2018/0116523 A1* | 5/2018 | Chatzistergos | ...... | A61B 5/1036 |

FOREIGN PATENT DOCUMENTS

| | | |
|---|---|---|
| JP | 2008086400 A | 4/2008 |
| WO | 2015099849 A1 | 7/2015 |

OTHER PUBLICATIONS

Zhao et al., "Floating autostereoscopic 3D display with multidimensional images for telesurgical visualization" International Journal of Computer Assisted Radiology and Surgery, 11, 207-215, published online Sep. 26, 2015 (Year: 2015).*

Japanese Intellectual Property Office, Final Office Action issued in Japanese Patent Application No. 2018-503521, dated Jun. 23, 2020, pp. 1-5.

* cited by examiner

Scan area 1

Scan area 2

Scan area 3

FULLY AUTOMATIC ULTRASONIC SCANNER AND SCAN DETECTION METHOD

CROSS REFERENCE TO RELATED APPLICATIONS

This application is a U.S. National Phase patent application of PCT Ser. No. PCT/CN2016/076081, filed Mar. 10, 2016, which claims priority to Chinese Patent Application Ser. No. 201510527764.0, filed Aug. 25, 2015, both of which are hereby incorporated by reference in the present disclosure in their entirety.

TECHNICAL FIELD

The present invention relates to medical equipment, and in particular to a fully automatic ultrasonic scanner and a scan detection method.

BACKGROUND ART

During breast cancer screening, a physician holds a probe of an existing hand-held ultrasonic breast scanner to carry out scanning (image data collection) and on-site diagnosis (image data analysis), which has the following technical problems:

1. the inspection must be performed by experienced professional physicians, and the inspection process is time-consuming;
2. the scan may not complete and may not cover the entire breast;
3. the detection effect depends on the physician's experience and physical condition and is instable; and
4. the image data cannot be stored and transmitted because of the non-standardized collection.

Therefore, hand-held breast ultrasonic methods are more suitable for treatment diagnosis instead of early screening. When breast cancer screening is popularized across the country, especially in rural areas or small and medium-sized cities, the expected effects for ultrasonic detection of early breast cancer cannot be achieved due to a lack of experienced professional physicians.

In addition, the basic requirements of breast ultrasonic inspection are as shown in FIG. 1: the patient needs to lie on the back during the inspection, and the ultrasonic probe should maintain close contact with the breast and be perpendicular to the skin surface during the scanning process. However, because the body shape and the size and shape of the organ of each person are not the same, the ultrasonic probe cannot make adjustment according to different curves of the human body. The current ultrasonic inspection is performed by a professional physician through a hand-held scanning probe or is performed according to a fixed shape, and it is difficult to adapt to various kinds of body shapes, breast sizes and compactness, thereby forming scan blind spots and resulting in missed diagnosis.

In the prior art, there is also a flexible part such as a water bag added between the skin surface of the to-be-detected organ and the ultrasonic probe; however, the ultrasonic probe is not in direct contact with the skin during detection, and the water bag between the probe and the skin causes multiple reflected interference images; and as the probe does not always keep perpendicular to the skin, the reflection angles of the collected images are different, which eventually lead to low-quality scanned images and the risk of missed diagnosis.

Therefore, a fully automatic scanner which can adaptively adjust the scan trace and probe angle according to different curves of the human body is urgently needed, to ensure that the ultrasonic probe scans against the skin surface and keeps perpendicular to the skin surface.

SUMMARY OF THE INVENTION

The objective of the present invention is to provide a fully automatic ultrasonic scanner and a scan detection method which can adaptively adjust the scan trace and probe angle according to different curves of the human body, so as to ensure that the ultrasonic probe scans against the skin surface and keeps perpendicular to the skin surface.

In order to solve the above-mentioned technical problems, the implementation manners of the present invention disclose a fully automatic ultrasonic scanner, comprising:
 an ultrasonic probe;
 a driving system for driving the ultrasonic probe to move; and
 a flexible structure on which the ultrasonic probe is mounted, wherein the flexible structure enables the ultrasonic probe to be always along a curve of a skin surface and keep perpendicular to the skin surface during scanning.

The implementation manners of the present invention further disclose a fully automatic ultrasonic scan detection method, comprising the steps of:
 performing scan using a fully automatic ultrasonic scanner which is along a curve of a skin surface and keeps perpendicular to the skin surface, to acquire N groups of two-dimensional images of a to-be-scanned organ, wherein N is an integer no less than 2; and
 reconstructing the acquired N groups of two-dimensional images to obtain three-dimensional stereo digital images.

Compared with the prior art, the main difference of the implementation manners of the present invention and the effect thereof lie in that:

the flexible structure of the fully automatic ultrasonic scanner has self-adaptive effect, and can adjust the scan trace and the probe angle in real time according to different curves of the human body, and ensure that the ultrasonic probe scans against the skin surface and keeps perpendicular to the skin surface, which improves the quality of the scanned images, and thereby enhances the detection rate and accuracy rate of early screening, and reduces the probability of missed diagnosis.

Further, by mounting the ultrasonic probe on a flexible track which is adjustable in elasticity, the ultrasonic probe is always along the curve of the skin surface and keeps perpendicular to the skin surface during scanning.

Further, in combination with the driving system and a first lifting support guide component, the ultrasonic probe is enabled to move left and right and at the same time move up and down and adjust the angle according to the contact with the skin, ensuring that the ultrasonic probe scans against the skin surface and keeps perpendicular to the skin surface. A compressed spring can realize the moving up and down of the ultrasonic probe against the to-be-detected organ, with no need of an additional guide rod lifting driving device, and therefore the structure is simple and easy to operate.

Further, a pressure sensor preloading structure can realize the moving up and down of the ultrasonic probe against the to-be-detected organ at an accurate pressure.

Further, a six-dimensional controllable mechanical arm is able to accurately control the ultrasonic probe to move up and down as well as left and right and adjust the angle.

Further, a fixing net can be used for fixing the to-be-detected organ and maintaining it in a certain shape, and at the same time can also avoid the flowing of the coupling liquid.

Further, the remote transmission and storage of the three-dimensional stereo digital images can realize remote medical diagnosis and long-term storage of data.

DETAILED DESCRIPTION

In the following statement, lots of technical details are proposed in order to make the readers better understand the present application. However, a person of ordinary skill in the art should understand that the technical solutions claimed by each claim of the present application can also be realized even without these technical details and various changes and modifications based on each of the following implementation manners.

In order to make the objectives, technical solutions and advantages of the present invention clearer, the implementation manners of the present invention will be further described in detail in conjunction with the accompanied drawings.

Figure 1:
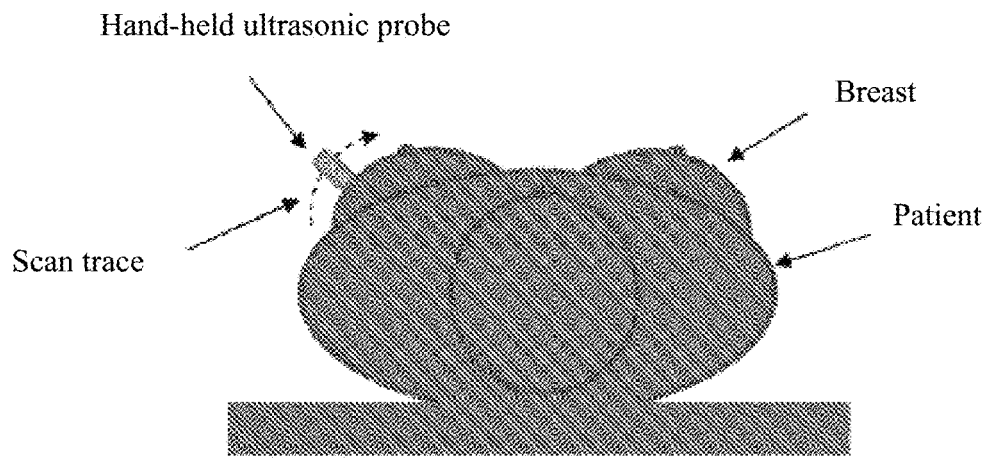
FIG. 1 is a schematic diagram of the basic requirements in breast ultrasonic inspection.
Figure 2:
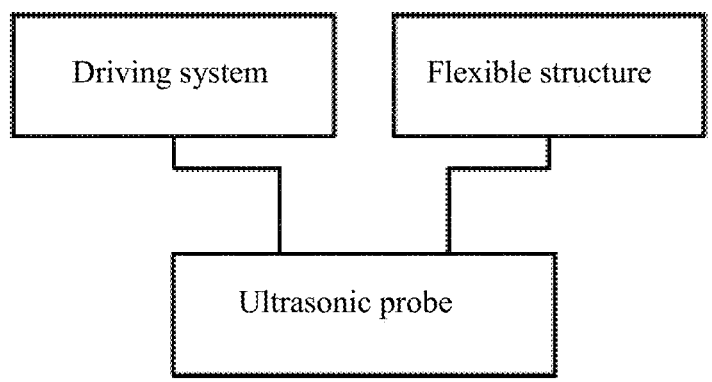
FIG. 2 is a schematic structural diagram of a fully automatic ultrasonic scanner in the first implementation manner of the present invention.

The first implementation manner of the present invention relates to a fully automatic ultrasonic scanner; and FIG. 2 is a schematic structural diagram of the fully automatic ultrasonic scanner, and the fully automatic ultrasonic scanner comprises:

an ultrasonic probe;
a driving system for driving the ultrasonic probe to move; and
a flexible structure on which the ultrasonic probe is mounted, wherein the flexible structure enables the ultrasonic probe to be always along a curve of a skin surface and keep perpendicular to the skin surface during scanning.

In the present implementation manner, the flexible structure of the fully automatic ultrasonic scanner has self-adaptive effect, can adjust the scan trace and probe angle in real time according to different curves of the human body, and ensure that the ultrasonic probe scans against the skin surface and keeps perpendicular to the skin surface, which improves the quality of the scanned images, and thereby enhances the detection rate and accuracy rate of early screening, and reduces the probability of missed diagnosis.

The second implementation manner to the fifth implementation manner below will provide four types of specific technical solutions to realize the above-mentioned flexible structure, so as to enable the ultrasonic probe to be always along the curve of the skin surface and keep perpendicular to the skin surface during scanning.

Figure 3:
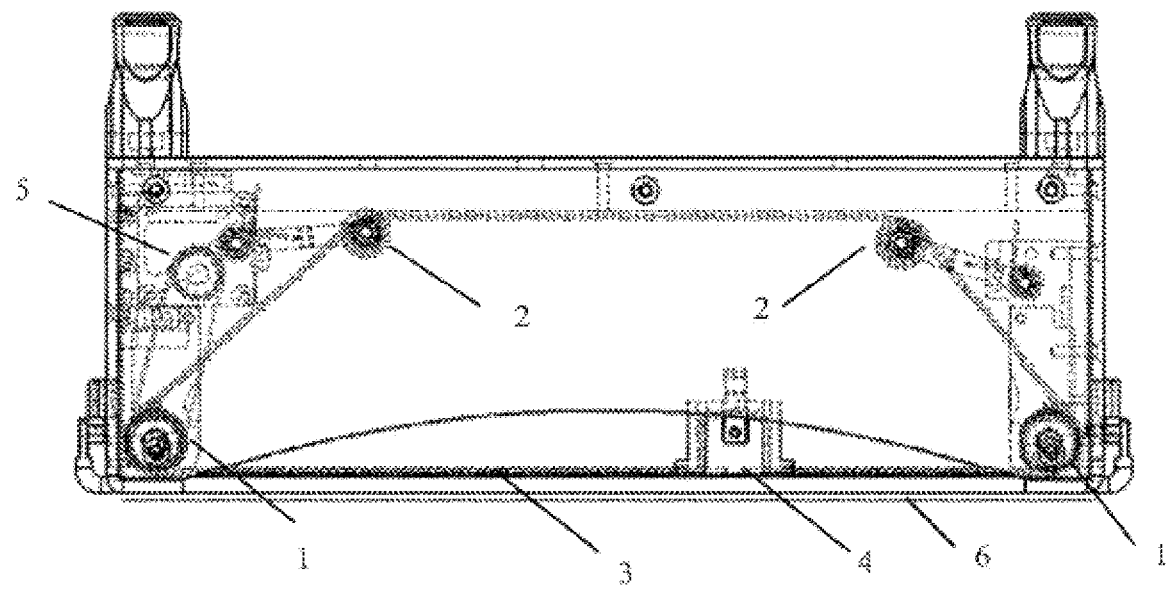
FIG. 3 is a schematic structural diagram of a fully automatic ultrasonic scanner in the second implementation manner of the present invention.

The second implementation manner of the present invention relates to a fully automatic ultrasonic scanner; and FIG. 3 is a schematic structural diagram of the fully automatic ultrasonic scanner. More specifically, the flexible structure comprises a flexible track 3 winding around a belt pulley 1 and a tension pulley 2, and the ultrasonic probe 4 is mounted on the flexible track 3, wherein the belt pulley 1 is connected to the driving system 5 to bring the flexible track 3 and the ultrasonic probe 4 to move;

the tension pulley 2 is used for adjusting the elasticity of the flexible track 3, to enable the flexible track 3 and the ultrasonic probe 4 to attach to the skin surface according to a shape of a to-be-detected organ.

The driving system 5 drives the flexible track 3 and the ultrasonic probe 4 which are attached to the skin surface to move left and right and move up and down along the skin during scanning.

It can be understood that because the track is flexible and adjustable in elasticity, and can deform according to the shape of the to-be-detected organ when being pressed against the skin, it can be ensured that the ultrasonic probe is in close contact with the skin and is perpendicular to the skin surface during scanning. The ultrasonic probe directly performing detection while in close contact with the skin will not cause interference images which lead to low-quality scanned images.

In addition, it can be understood that the to-be-scanned organ can be superficial tissues and organs like breasts, thyroid, limbs, and truncus, etc.

Preferably, a fixing net 6 for fixing the to-be-detected organ is further comprised. The fixing net can be used for fixing the to-be-detected organ and maintaining it in a certain shape, and at the same time can also avoid the flowing of the coupling liquid.

Figure 4:
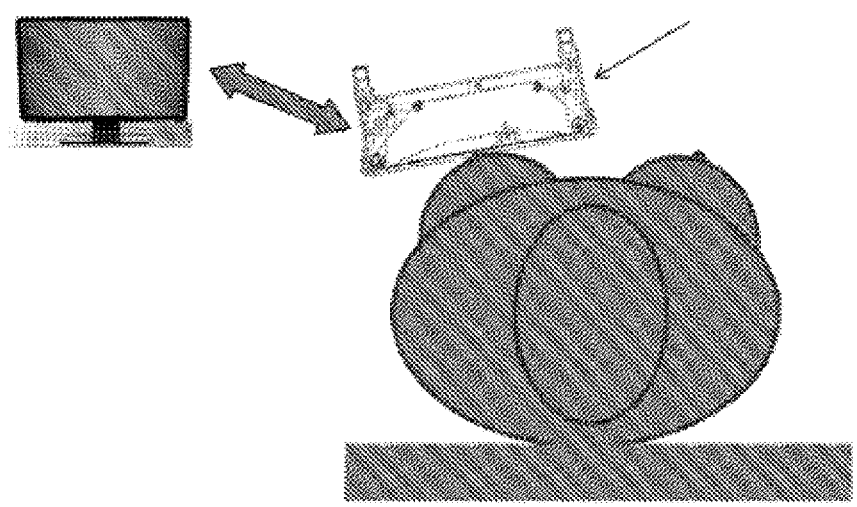
FIG. 4 is a schematic diagram of a breast scan application scenario of a fully automatic ultrasonic scanner composed by a flexible track in the second implementation manner of the present invention.

What is shown in FIG. 4 is a schematic diagram of a breast scan application scenario of a fully automatic ultrasonic scanner composed by a flexible track. The ultrasonic probe is mounted inside the mechanical scanning device, and the driving system drives the ultrasonic probe to move left and right and move up and down along the shape of the breast. The operator places the scanning device on the breast, starts the scanning device to enable the ultrasonic probe to move left and right on the breast to acquire breast ultrasonic information, and obtains three-dimensional breast ultrasonic images by way of computer conversion.

In addition, in other implementation manners of the present invention, the way of realizing the flexible structure through the flexible track is not limited to the way shown in FIG. 3, and a person skilled in the art can also make various variations or modifications to realize the flexible structure through the flexible track.

For example, the flexible track shown in FIG. 3 is a circulating structure with its head and tail connected, while in another preferable example, it is also possible to not connect the head and tail of the flexible track, but instead winding the flexible track directly around the trolley or the belt pulley driven by the driving system, which likewise can realize the above-mentioned function.

For another example, the flexible track shown in FIG. 3 adjusts the elasticity through the tension pulley, and the tension pulley is located inside the loose side of the flexible track, while in another preferable example, a person skilled in the art can absolutely make equivalent substitutions for the position of the tension pulley, and can also absolutely replace the tension pulley with other parts to adjust the elasticity or realize adjustment through the elasticity of the flexible track itself.

Figure 5:
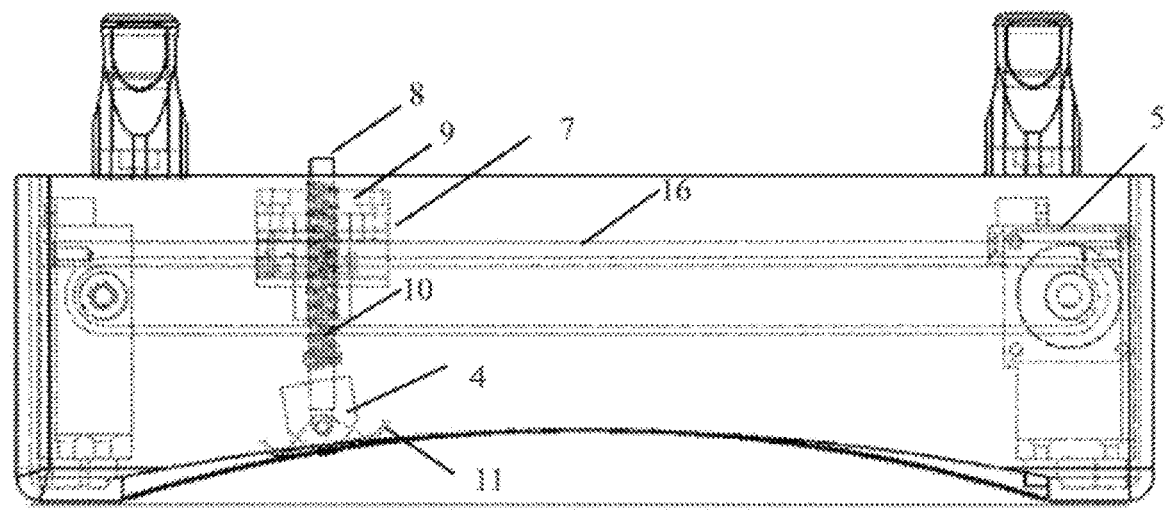
FIG. 5 is a schematic structural diagram of a fully automatic ultrasonic scanner in the third implementation manner of the present invention.

The third implementation manner of the present invention relates to a fully automatic ultrasonic scanner; and FIG. 5 is a schematic structural diagram of the fully automatic ultrasonic scanner.

The third implementation manner is another implementation manner for realizing the flexible structure. In the third implementation manner, in combination with the driving system and the first lifting support guide component, the ultrasonic probe is enabled to move left and right and at the same time move up and down and adjust the angle according to the contact with the skin, ensuring that the ultrasonic probe scans against the skin surface and keeps perpendicular to the skin surface. Moreover, the compressed spring in the first lifting support guide component can realize the moving up and down of the ultrasonic probe against the to-be-detected organ, with no need of an additional guide rod lifting driving device, and therefore the structure is simple and easy to operate. More specifically, the flexible structure comprises a first lifting support guide component 7, wherein a bottom end of the first lifting support guide component 7 is mounted with an ultrasonic probe 4, and the first lifting support guide component 7 is used for adjusting lifting of the ultrasonic probe and for guiding an angle of the ultrasonic probe.

The driving system 5 is used for driving the first lifting support guide component 7 to move left and right as a whole, so as to bring the ultrasonic probe 4 to move left and right.

The first lifting support guide component 7 comprises a guide rod 8, a bearing 9, a compressed spring 10 and a guide probe cap 11.

The guide rod 8 vertically passes through an inner ring of the bearing 9, and a bottom end of the guide rod 8 is connected to the ultrasonic probe 4.

One end of the compressed spring 10 is fastened to the bearing 9, and the other end is fastened to the guide rod 8. The compressed spring 10 is used for correspondingly conducting contraction and relaxation according to pressure changes between the ultrasonic probe at the bottom end of the guide rod and the skin, to bring the guide rod to move up and down so as to keep the ultrasonic probe always against the skin surface.

Preferably, one end of the compressed spring 10 is fastened to an inner ring of the bearing 9, and the other end is fastened to a lower end of the guide rod 8, which is more beneficial to the compressed spring for realizing contraction and relaxation. It is certain that in other implementation manners of the present invention, the compressed spring can also be provided in another position that is not limited herein, as long as it can perform corresponding contraction and relaxation according to the pressure change.

The guide probe cap 11 rotates according to ups and downs of the skin to keep tangent to the skin surface and bring the ultrasonic probe 4 to rotate synchronously, so as to adjust the angle of the ultrasonic probe to keep it perpendicular to the skin surface.

According to the above description, it can be understood that the first lifting support guide component 7 on one hand is used for adjusting the lifting (i.e. moving up and down) of the ultrasonic probe and on the other hand is used for guiding the angle of the ultrasonic probe, wherein the guide rod 8, the bearing 9 and the compressed spring 10 are used for adjusting the lifting of the ultrasonic probe; and the guide probe cap 11 is used for adjusting the angle of the ultrasonic probe.

To facilitate the understanding, it should be additionally noted that the working principle of the compressed spring is mainly as follows:

when the pressure between the ultrasonic probe and the skin increases, the guide rod moves up and brings the compressed spring to contract upward; and when the pressure between the ultrasonic probe and the skin decreases, the elasticity of the compressed spring makes the compressed spring relax downward and bring the guide rod to move down.

Accordingly, the compressed spring is able to adaptively adjust the contraction and relaxation of the compressed spring according to pressure changes between the ultrasonic probe at the bottom end of the guide rod and the skin to bring the guide rod to move up and down, so as to keep the ultrasonic probe always against the skin surface.

Figure 6:
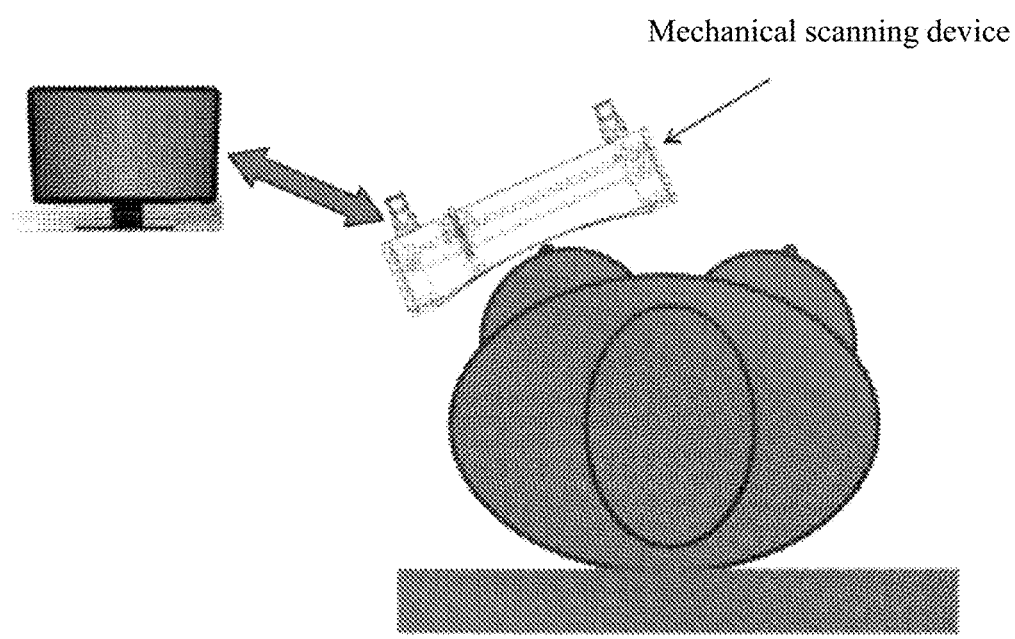
FIG. 6 is a schematic diagram of a breast scan application scenario of a fully automatic ultrasonic scanner composed by a flexible track in the third implementation manner of the present invention.

What is shown in FIG. 6 is a schematic diagram of a breast scan application scenario of a fully automatic ultrasonic scanner composed by a first lifting support guide component. The ultrasonic probe is mounted inside the mechanical scanning device driven by the driving system.

The first lifting support guide component 7 and the driving system 5 realize the moving up and down as well as left and right of the probe, the compressed spring realizes the moving up and down of the probe against the breast at an approximately fixed pressure, and the probe and the probe cap are easy to remove, and the structure is easy for cleaning. The operator places the scanning device on the breast, starts the scanning device to enable the ultrasonic probe to move back and forth on the breast to acquire breast ultrasonic information, and obtains three-dimensional breast ultrasonic images by way of computer conversion.

Figure 7:
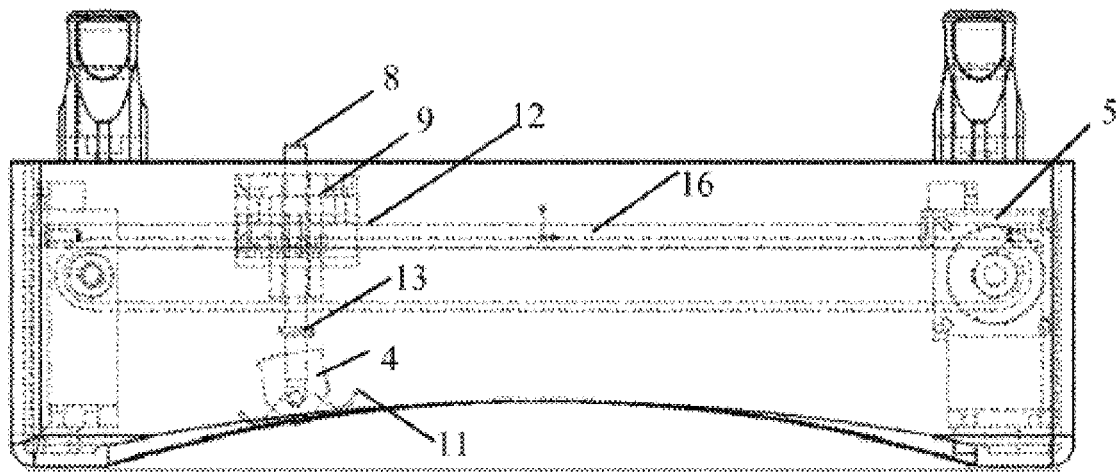
FIG. 7 is a schematic structural diagram of a fully automatic ultrasonic scanner in the fourth implementation manner of the present invention.

The fourth implementation manner of the present invention relates to a fully automatic ultrasonic scanner; and FIG. 7 is a schematic structural diagram of the fully automatic ultrasonic scanner.

The fourth implementation manner is basically the same as the third implementation manner, and the main difference lies in that: in the third implementation manner, the first lifting support guide component comprises a guide rod, a bearing, a compressed spring and a guide rod cap, and the compressed spring correspondingly conducts contraction and relaxation according to pressure changes between the ultrasonic probe at the bottom end of the guide rod and the skin, to bring the guide rod to move up and down so as to keep the ultrasonic probe always against the skin surface.

However, in the fourth implementation manner, a pressure sensor preloading structure can realize the moving up and down of the ultrasonic probe against the to-be-detected organ at an accurate pressure. More specifically, as shown in FIG. 7, the flexible structure comprises a second lifting support guide component 12, wherein a bottom end of the second lifting support guide component 12 is mounted with an ultrasonic probe 4, and the second lifting support guide component 12 is used for adjusting lifting of the ultrasonic probe and for guiding the angle of the ultrasonic probe.

The driving system 5 is used for driving the second lifting support guide component 12 to move left and right as a whole, so as to bring the ultrasonic probe to move left and right.

The second lifting support guide component 12 comprises a guide rod 8, a bearing 9, a pressure sensor preloading structure 13 and a guide probe cap 11.

The guide rod 8 vertically passes through an inner ring of the bearing 9, and a bottom end of the guide rod 8 is connected to the ultrasonic probe 4.

The pressure sensor preloading structure 13 comprises a pressure sensor and a guide rod lifting driving device.

The pressure sensor detects the pressure of the skin against the ultrasonic probe and outputs a pressure signal.

The guide rod lifting driving device drives the guide rod 8 to ascend or descend according to the pressure signal, so as to keep the ultrasonic probe always against the skin surface.

The guide probe cap 11 rotates according to ups and downs of the skin to keep tangent to the skin surface and bring the ultrasonic probe to rotate synchronously, so as to adjust the angle of the ultrasonic probe to keep it perpendicular to the skin surface.

In addition, it can be understood that if the pressure signal acquired by the pressure sensor preloading structure is greater than a predetermined pressure value, i.e. the ultrasonic probe and the skin are too close, then the guide rod lifting driving device drives the guide rod to contract, thereby lifting the ultrasonic probe upward to a higher position; and if the pressure signal acquired by the pressure sensor preloading structure is smaller than the predetermined pressure value, i.e. the ultrasonic probe is not in close contact with the skin or is not in contact with the skin, then the guide rod lifting driving device drives the guide rod to stretch, thereby pressing the ultrasonic probe downward to a lower position.

Preferably, the outer layer of the guide rod is provided with a first gear, and the guide rod lifting driving device comprises a driving controller, a rotation driving motor, and a gear driving plate, wherein the periphery of the gear driving plate is provided with a second gear matching the first gear; and the driving controller is connected to the pressure sensor and drives the rotation driving motor according to the pressure signal, so as to bring the second gear to rotate forward or backward, thereby bringing the first gear to realize the ascending or descending of the guide rod, so as to adjust the height of the ultrasonic probe.

In addition, it can be understood that in other embodiments of the present invention, there can be a plurality of gear driving plates, which are all connected to the rotation driving motor to together bring the first gear at the outer layer of the guide rod.

In addition, in other implementation manners of the present invention, the guide rod lifting driving device can also be implemented by other ways. For example, the guide rod is directly connected to the rotation driving motor, and the guide rod is driven by the motor to rotate clockwise or anticlockwise. Moreover, an outside surface of the guide rod is provided with an external thread, and the external thread matches an internal thread in the bearing, so as to realize the lifting of the guide rod when the guide rod is driven by the motor to rotate clockwise or anticlockwise.

Preferably, the driving system 5 comprises a driving motor, a belt pulley and a belt, and a horizontal guide rod 16.

The belt pulley is driven by the driving motor, and the belt is wound around the belt pulley; preferably, the driving motor is a stepping motor.

The first lifting support guide component or the second lifting support guide component is horizontally provided with a guide pipeline to cooperatively slide with the horizontal guide rod 16.

Moreover, the first lifting support guide component or the second lifting support guide component is connected to the belt, so that the lifting support guide component is brought to horizontally slide along the horizontal guide rod and move left and right when the belt moves.

Figure 8:
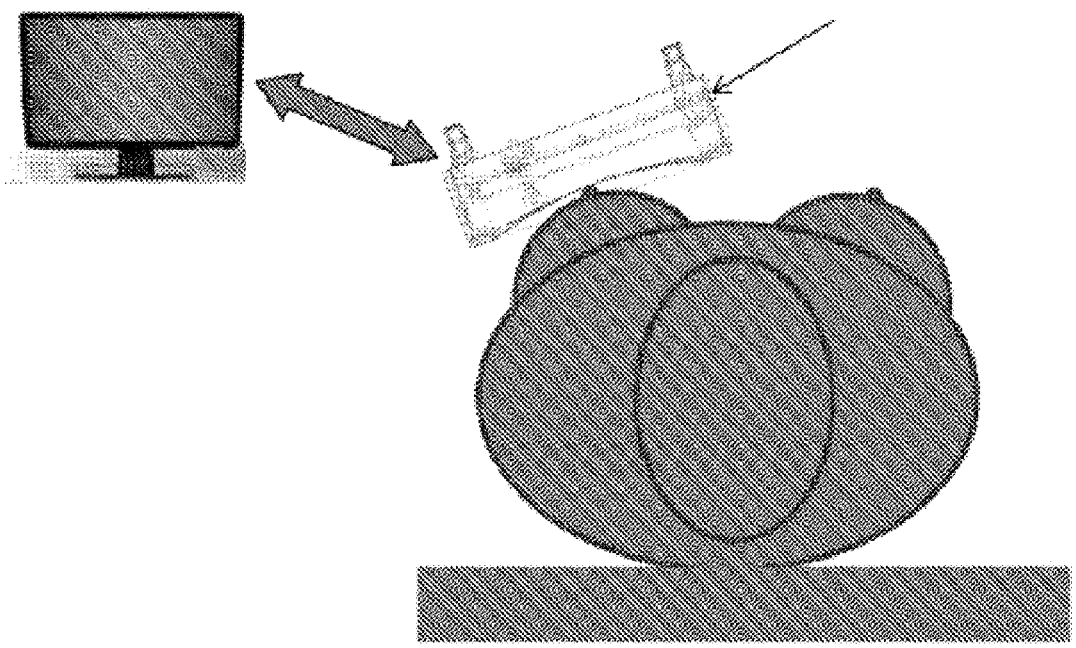
FIG. 8 is a schematic diagram of a breast scan application scenario of a fully automatic ultrasonic scanner composed by a flexible track in the fourth implementation manner of the present invention.

What is shown in FIG. 8 is a schematic diagram of a breast scan application scenario of a fully automatic ultrasonic scanner composed by a second lifting support guide component. The ultrasonic probe is mounted inside the mechanical scanning device driven by the driving system.

The ultrasonic probe is mounted inside the mechanical scanning device driven by the driving system. The second lifting support guide component 12 and the driving system 5 realize the moving up and down as well as left and right of the probe and realize the moving left and right as well as up and down of the ultrasonic probe, the pressure sensor preloading structure realizes the moving up and down of the probe against the breast at an accurate pressure, and the probe and the probe cap are easy to remove and clean. The operator places the scanning device on the breast, starts the scanning device to enable the ultrasonic probe to move back and forth on the breast to acquire breast ultrasonic information, and obtains three-dimensional breast ultrasonic images by way of computer conversion.

Figure 9:
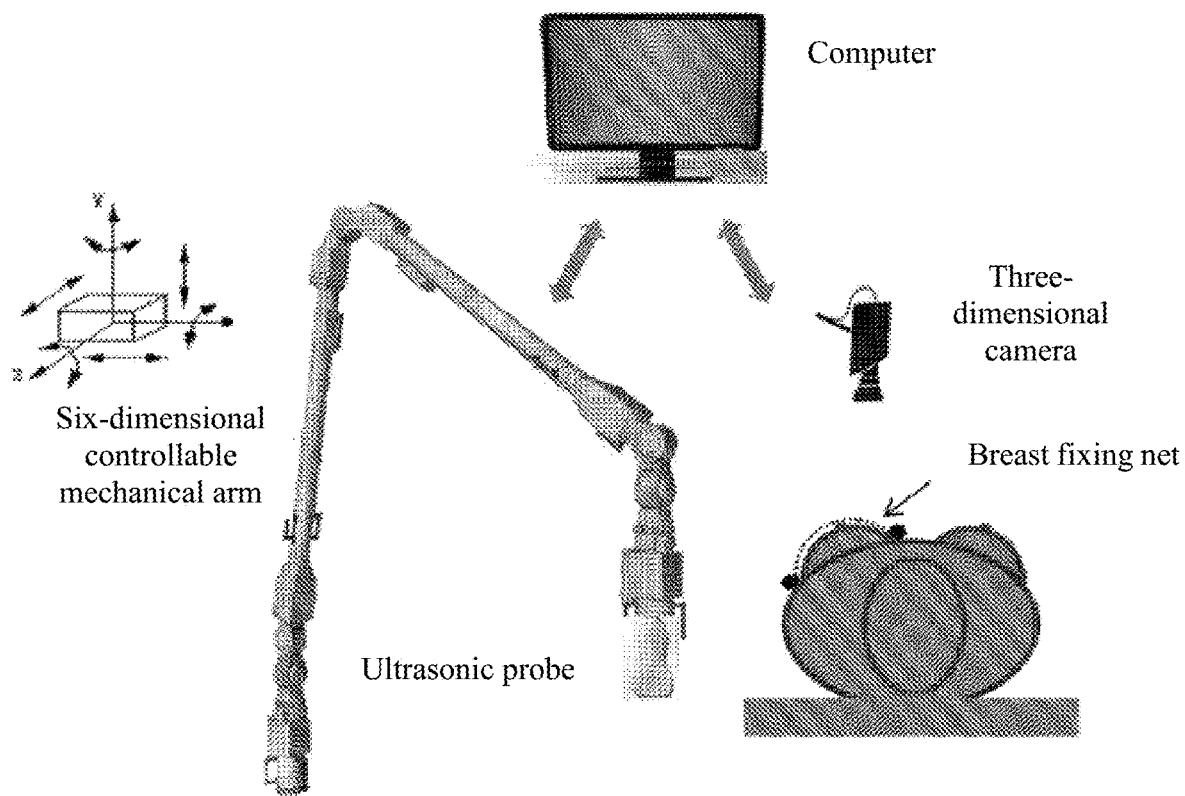
FIG. 9 is a schematic structural diagram of a fully automatic ultrasonic scanner in the fifth implementation manner of the present invention.

The fifth implementation manner of the present invention relates to a fully automatic ultrasonic scanner; and FIG. 9 is a schematic structural diagram of the fully automatic ultrasonic scanner. The fifth implementation manner is another implementation manner for realizing the flexible structure, and more specifically, a laser three-dimensional camera is further comprised, and the laser three-dimensional camera is used for shooting and transmitting three-dimensional images of a to-be-scanned organ.

The flexible structure comprises a controllable mechanical arm, and an end part of the controllable mechanical arm is mounted with the ultrasonic probe.

The mechanical arm adjusts a position and an angle of the ultrasonic probe according to the three-dimensional images of the to-be-scanned organ, to enable the ultrasonic probe to be always along the curve of the skin surface and keep perpendicular to the skin surface during scanning.

Preferably, the mechanical arm is a six-dimensional controllable mechanical arm that is able to accurately control the ultrasonic probe to move up and down as well as left and right and adjust the angle.

As shown in the figure, in the breast scan application scenario of the fully automatic ultrasonic scanner composed by the controllable mechanical arm, the breast is fastened by a tightened net, and a three-dimensional imaging system (a three-dimensional camera) is used to shoot and acquire the three-dimensional shape of the breast. The ultrasonic probe is mounted on a six-dimensional controllable mechanical arm. The mechanical arm is controlled by a computer to scan according to the three-dimensional shape of the breast, so as to acquire three-dimensional breast ultrasonic images.

The above second to the fifth implementation manners describe in detail the specific technical solutions for realizing the flexible structure in the first implementation manner, and the scan detection method based on each of the above-mentioned fully automatic ultrasonic scanners will be introduced in detail below.

The sixth implementation manner of the present invention relates to a fully automatic ultrasonic scan detection method. The fully automatic ultrasonic scan detection method comprises the steps of:

step S1, performing scan using the fully automatic ultrasonic scanner of any one of the first implementation manner to the fifth implementation manner which is along a curve of a skin surface and keeps perpendicular to the skin surface, to acquire N groups of two-dimensional images of a to-be-scanned organ, wherein N is an integer no less than 2; and step S2, reconstructing the acquired N groups of two-dimensional images to obtain three-dimensional stereo digital images.

When the fully automatic ultrasonic scanner is used to perform scan, the scan trace and angle can be adjusted in real time according to different curves of the human body to keep the scanner probe always along the skin surface and perpendicular to the skin surface, which can automatically adapt to the physiological characteristics of various patients, and at the same time realize data collection standardization and reduce misdiagnosis and missed diagnosis.

Figure 10:
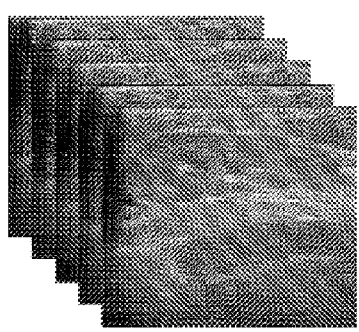
FIG. 10 is a series of two-dimensional images generated by scanning in the sixth implementation manner of the present invention.
Figure 10:
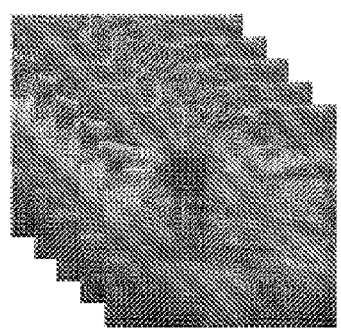
Figure 10:
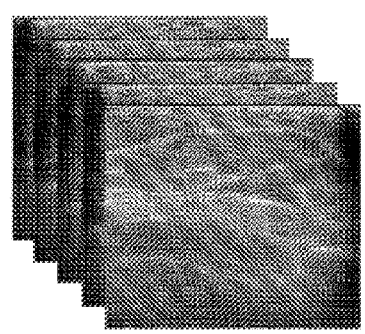

In addition, it can be understood that the inspection should be carried out in N groups, usually 2 to 3 groups, during an automatic scan since the width of the ultrasonic probe is limited, and the scan of each group will collect more than 300 images, forming mass data. What is shown in FIG. 10 is a series of two-dimensional images generated by scanning, wherein three groups of two-dimensional images are generated for three different scan areas.

Figure 11:
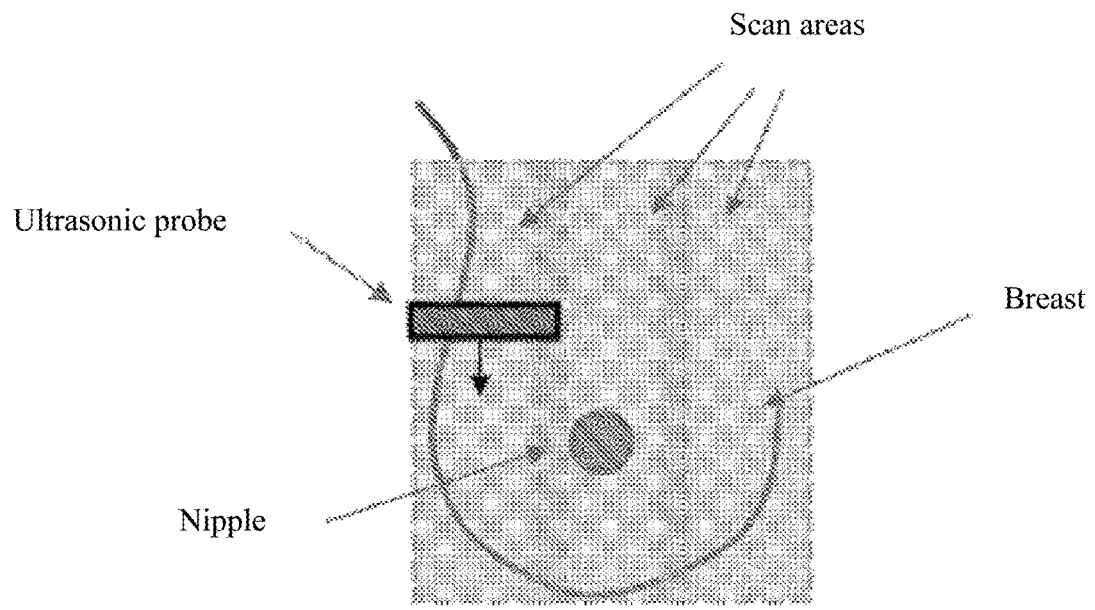
FIG. 11 is a schematic diagram of longitudinal scanning in the sixth implementation manner of the present invention.
Figure 12:
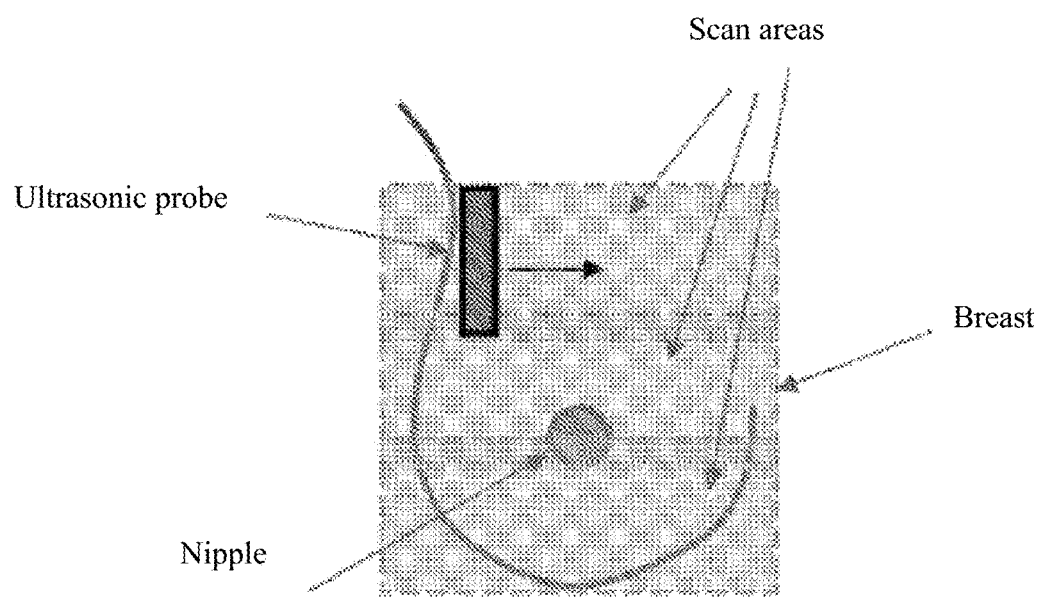
FIG. 12 is a schematic diagram of transverse scanning in the sixth implementation manner of the present invention.

Preferably, in step S1, scan directions comprise longitudinal scan and transverse scan, respectively as shown in FIG. 11 and FIG. 12. From the perspective of clinical diagnosis, the two scan modes are equivalent and can be freely selected according to the convenience of actual operation.

Preferably, before step S1, the following step is further comprised:

setting the fully automatic ultrasonic scanner, wherein the setting comprises a pressure threshold between the ultrasonic probe and the skin during scanning, a scan direction, and the group number N of scanned two-dimensional images.

Figure 13:
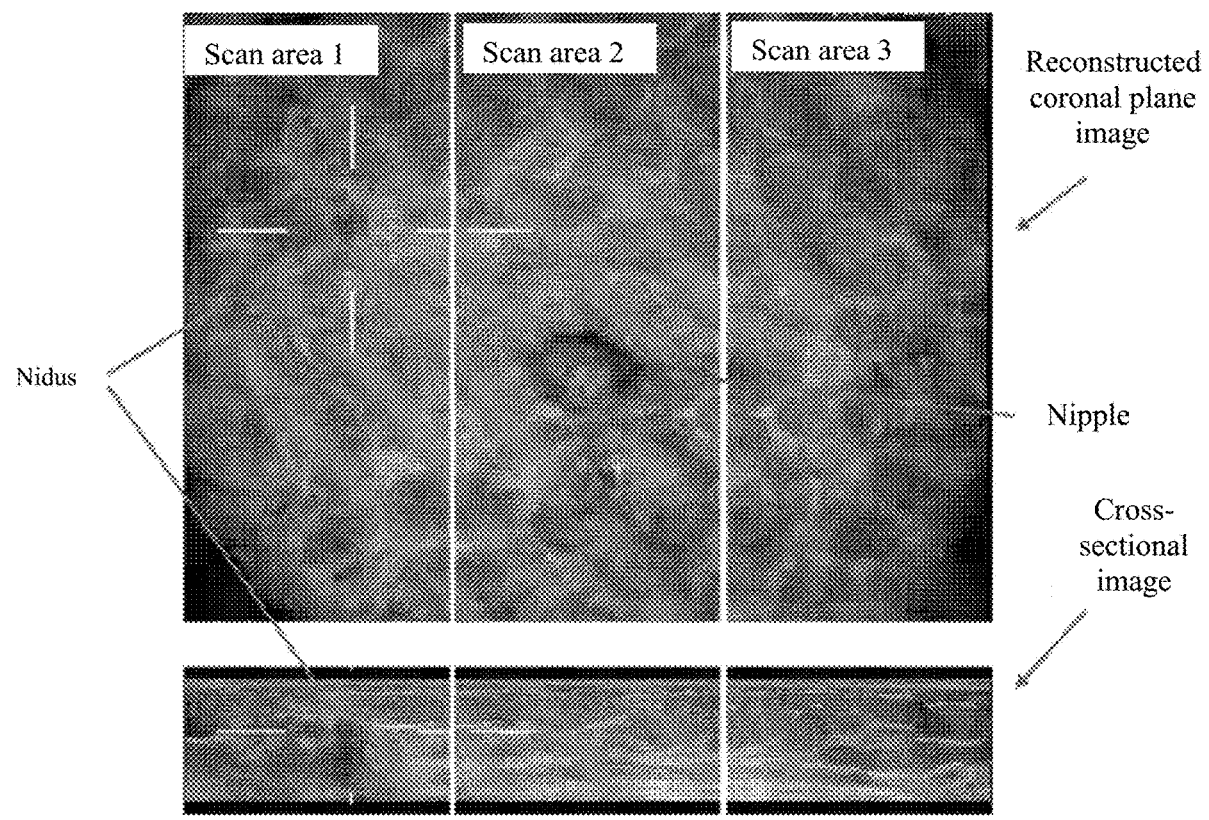
FIG. 13 are reconstructed three-dimensional stereo images in the sixth implementation manner of the present invention.

Preferably, in step S2, the three-dimensional stereo digital images obtained through reconstruction comprise reconstructed coronal plane images and cross-sectional images. What are shown in FIG. 13 are three-dimensional reconstructed stereo images.

Preferably, after step S2, the following step is further comprised: performing remote transmission and storage of the three-dimensional stereo digital images, thereby realizing remote medical diagnosis and long-term storage of data.

Figure 14:
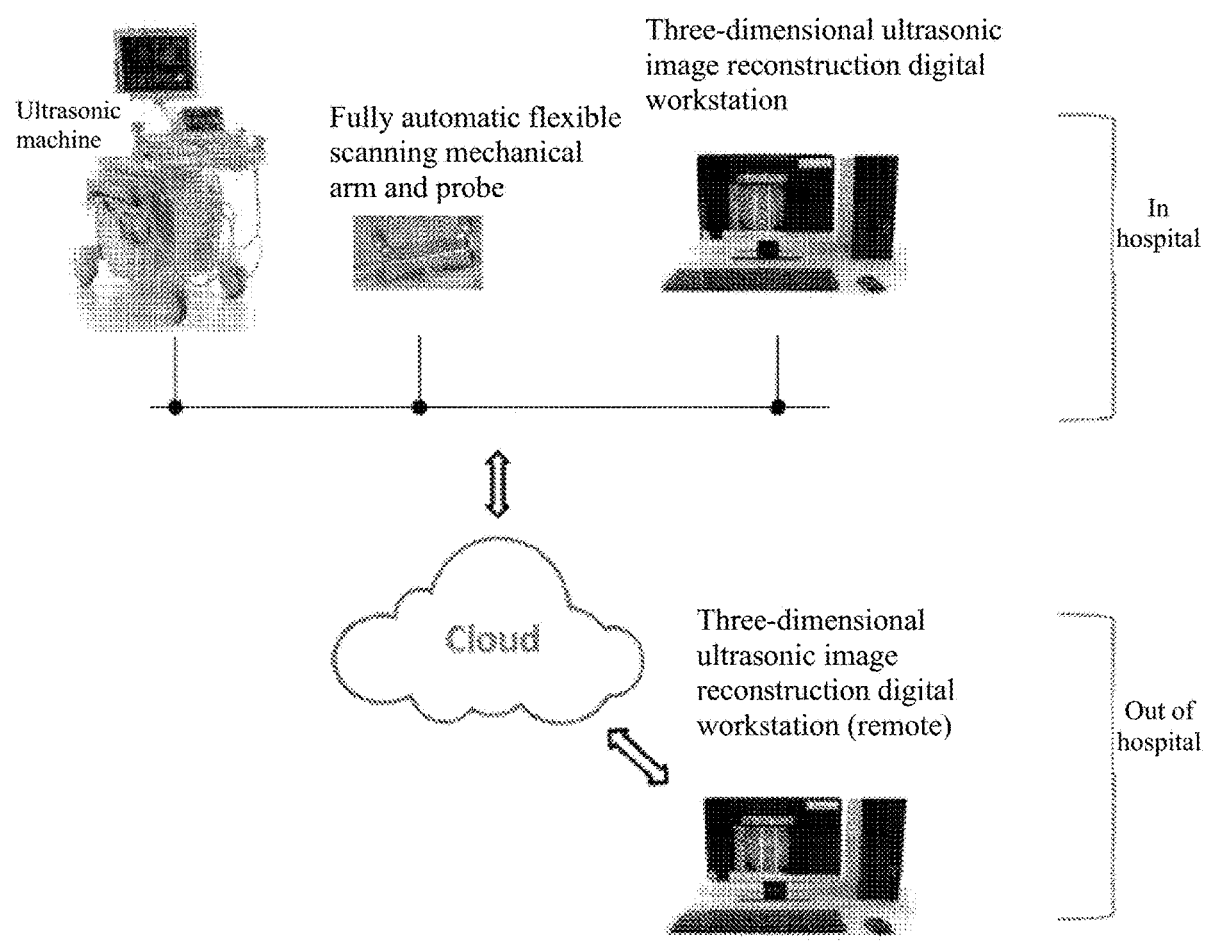
FIG. 14 is a work flow diagram of fully automatic breast ultrasonic scan detection in the sixth implementation manner of the present invention.

As a preferable example, the work flow of fully automatic breast ultrasonic scan detection is as shown in FIG. 14. Because the data collection in the traditional hand-held ultrasonic method is non-standardized, the physician can only review and diagnose on site, and thus the separation of inspection and diagnosis cannot be realized; and the collected data likewise cannot be stored for lookup and comparison afterwards. However, the automatic scan controlled by a computer as shown in FIG. 14 makes data collection standardized, and reconstructs, by way of processing via an image digital workstation, the two-dimensional images collected by the above automatic computer scan into three-dimensional stereo digital images for review and diagnose by the physician, which can realize remote medical diagnosis and long-term storage of data files.

In summary, one of the difficulties for computer controlled automatic scan is how to adjust the scan trace and probe angle in real time according to different curves of the human body, to keep close contact with the breast and in an angle perpendicular with the skin surface.

For this technical difficulty, the present invention on one hand develops a fully automatic flexible scanner. Because the probe is flexible, it can automatically adapt to various kinds of body shapes, breast sizes and breast compactness of women (especially Asian and Chinese women), and at the same time avoid the scan blind spot, thus truly achieving full-breast no-blind-spot scanning, thereby improving the image quality and realizing image standardization, and improving the detection rate and accuracy rate of early screening.

On the other hand, by implementing computer controlled fully automatic scan to separate image data collection (inspection) from image data analysis (diagnosis) of the breast ultrasonic process, the inspection does not need a professional physician to operate, which saves the precious time of the professional physician, thus lowering the inspection cost and reducing the demand for experienced professional physicians; the scan can ensure full coverage of the breast and reduce the probability of missed diagnosis; and the realization of automation and standardization of image data collection not only makes the operator's experience and physical condition irrelevant and reduces missed diagnosis and misdiagnosis, but also makes it possible to store the collected image data for a long time and transmit the same remotely, thereby realizing remote diagnosis and the review as well as analysis and comparison afterwards.

In addition, it should be understood that after reading the above-mentioned content of the present invention, a person skilled in the art can make various changes or modifications to the present invention, and these equivalent forms as well fall into the scope defined by the claims attached in the present application.

It is to be noted that in the claims and the specification of the present patent, relation terms such as the first and the second, etc. are merely used for differentiating one entity or operation from another entity or operation, and do not necessarily require or imply any of these practical relations or sequences between these entities or operations. Moreover, the term "comprise", "include" or any other variants thereof is intended to cover a non-exclusive inclusion, which makes a process, method, item or device including a series of elements not only include those elements, but also include other elements that are not explicitly listed, or also include the elements inherent for the process, method, item or device. In the absence of more restrictions, the element defined by the statement "comprise a" does not rule out other identical elements in the process, method, item or device including the elements.

Though the present invention is illustrated and described by referring to some preferential implementation manners of the present invention, a person of ordinary skill in the art should understand that various changes can be made thereto in form and in detail without departing from the spirit and scope of the present invention.

The invention claimed is:

1. An ultrasonic scanner for scanning on a skin surface that is over any one of a plurality of to-be-detected organs, each of the plurality of to-be-detected organs coming from a different person, the ultrasonic scanner capable of being used by placement directly on the skin surface or with a coupling liquid that is flowable and disposed on the skin surface to provide a medium for the transmission of acoustic signals to the skin surface and collected image signals from the skin surface, the ultrasonic scanner comprising:
   an ultrasonic probe that scans along a curve of the skin surface above the one of the plurality of to-be-detected organs, the ultrasonic probe generating and transmitting the acoustic signals and receiving the collected image signals;
   a flexible and movable belt on which the ultrasonic probe is mounted;
   a driving system for driving the flexible and moveable belt with the ultrasonic probe mounted thereon, the driving system including a belt pulley and a tension pulley that assist, along with the coupling liquid disposed between the flexible and moveable belt and the skin surface, in maintaining the ultrasonic probe moving along and in close contact with the skin surface, as well as perpendicular to the skin surface during scanning of the to-be-detected organ of the plurality of to-be-detected organs, thereby maintaining a consistent reflection angle for the received collected image signals and reducing interference images; and
   wherein the flexible and moveable belt winds around the belt pulley and the tension pulley, and
   wherein the belt pulley is connected to the driving system to move the flexible and moveable belt and the ultrasonic probe disposed thereon and which further contains two belt pulley wheels between which is disposed a portion of the flexible and moveable belt to which the ultrasonic probe is mounted and which moves along in close contact with the skin surface.

2. An ultrasonic scan detection method, comprising the steps of:
   performing a scan, using the ultrasonic scanner according to claim 1, by initiating operation of the ultrasonic scanner, including initiating the driving system to move the ultrasonic probe along the curve of the skin surface and keeping perpendicular to the skin surface, to acquire N groups of two-dimensional images of a to-be-scanned organ, wherein N is an integer no less than 2; and
   reconstructing the acquired N groups of two-dimensional images to obtain three-dimensional stereo digital images.

3. The ultrasonic scanner method according to claim 2, further comprising the step of attaching a fixing net over the skin surface using the coupling liquid for fixing the to-be-detected organ in position prior to the step of performing the scan.

4. The ultrasonic scan detection method according to claim 2, characterized in that the three-dimensional stereo digital images obtained through reconstruction comprise reconstructed coronal plane images and cross-sectional images.

5. The ultrasonic scan detection method according to claim 2, characterized in that directions of the scan comprise transverse scan direction and vertical scan direction in the step of performing the scan using the ultrasonic scanner which is along the curve of the skin surface and keeps perpendicular to the skin surface.

6. The ultrasonic scan detection method according to claim 2, further comprising the step of:
   performing remote transmission and storage of the three-dimensional stereo digital images.

7. The ultrasonic scan detection method according to claim 2, wherein, before the step of performing scan using the ultrasonic scanner which is along the curve of the skin surface and keeps perpendicular to the skin surface, further comprising the step of:
   setting the ultrasonic scanner, wherein the setting comprises setting a pressure threshold between the ultrasonic probe and the skin during scanning, setting a scan direction, and setting the group number N of scanned two-dimensional images.

8. The ultrasonic scan detection method according to claim 2, wherein after the step of performing the scan by moving the ultrasonic probe along the skin surface, another scan is performed by moving the ultrasonic probe to another skin surface that is different in shape than the skin surface and initiating another operation of the ultrasonic scanner, including initiating the driving system to move the ultrasonic probe along another curve of the another skin surface and keeping perpendicular to the another skin surface, to acquire another N groups of two-dimensional images of another to-be-scanned organ, wherein N is an integer no less than 2.

9. An ultrasonic scan detection method, comprising the steps of:
   exposing the skin surface that is disposed over the one of the plurality of to-be-detected organs
   applying a coupling liquid that is flowable on the exposed skin surface that is disposed over the one of the plurality of to-be-detected organs;
   setting the portion of the flexible and moveable belt to which the ultrasonic probe is mounted that is disposed between the two belt pulley wheels over the exposed skin surface that is disposed over the one of the plurality of to-be-detected organs and to which the coupling liquid has been applied;
   performing a scan using the ultrasonic scanner according to claim 1, by initiating operation of the ultrasonic scanner, including initiating the driving system to move the ultrasonic probe along the curve of the skin surface and keeping perpendicular to the skin surface, to acquire N groups of two-dimensional images of a to-be-scanned organ, wherein N is an integer no less than 2; and
   reconstructing the acquired N groups of two-dimensional images to obtain three-dimensional stereo digital images.

10. The ultrasonic scan detection method according to claim 9, characterized in that directions of the scan comprise transverse scan direction and vertical scan direction in the step of performing the scan using the fully automatic ultrasonic scanner which is along the curve of the skin surface and keeps perpendicular to the skin surface.

11. The ultrasonic scan detection method according to claim 10, wherein, before the step of performing scan using the ultrasonic scanner which is along the curve of the skin surface and keeps perpendicular to the skin surface, further comprising the step of:
- setting the ultrasonic scanner, wherein the setting comprises setting a pressure threshold between the ultrasonic probe and the skin during scanning, setting a scan direction, and setting the group number N of scanned two-dimensional images, and
- wherein during the scan, the movement of the ultrasonic probe on the skin surface is fully automatic and maintains the pressure threshold between the ultrasonic probe and the skin during scanning.

12. The ultrasonic scan detection method according to claim 9, wherein after the step of performing the scan by moving the ultrasonic probe along the skin surface, another scan is performed by moving the ultrasonic probe to another skin surface that is different in shape than the skin surface and initiating another operation of the ultrasonic scanner, including initiating the driving system to move the ultrasonic probe along another curve of the another skin surface and keeping perpendicular to the another skin surface, to acquire another N groups of two-dimensional images of another to-be-scanned organ, wherein N is an integer no less than 2.

* * * * *